United States Patent [19]

Frisch et al.

[11] 4,198,505

[45] Apr. 15, 1980

[54] PREPARATION OF TRIS-($\beta$-HYDROXYPROPYL) ISOCYANURATE

[75] Inventors: Kurt C. Frisch, Detroit, Mich.; Daniël M. J. Tummers; Anne Te Nijenhuis, both of Geleen, Netherlands

[73] Assignee: Stamicarbon, B.V., Geleen, Netherlands

[21] Appl. No.: 4,476

[22] Filed: Jan. 18, 1979

[30] Foreign Application Priority Data

Jan. 23, 1978 [NL] Netherlands .......................... 7800770

[51] Int. Cl.$^2$ ............................................ C07D 251/34
[52] U.S. Cl. .................................................... 544/221
[58] Field of Search ............................................ 544/221

[56] References Cited

U.S. PATENT DOCUMENTS 4,063,020  12/1977  den Otter et al. .................... 544/221

*Primary Examiner*—John M. Ford
*Attorney, Agent, or Firm*—Cushman, Darby & Cushman

[57] ABSTRACT

An improved process for the preparation of tris-($\beta$-hydroxypropyl) isocyanurate by the reaction of propylene oxide with cyanuric acid. Propylene oxide and cyanuric acid are reacted at a temperature of between about 100° and 150° C. at an elevated pressure, and in the absence of a catalyst, in a reaction medium of a polyhydroxy compound which is a liquid at the reaction temperature and in which the tris-($\beta$-hydroxypropyl) isocyanurate is soluble or with which it is miscible.

8 Claims, No Drawings

PREPARATION OF TRIS-(β-HYDROXYPROPYL) ISOCYANURATE

BACKGROUND OF THE INVENTION

It has been previously proposed to prepare tris-(β-hydroxypropyl) isocyanurate by reaction of cynauric acid with an alkylene oxide. Inasmuch as cyanuric acid is a solid at the reaction temperature, the reaction is carried out in an inert solvent or vehicle such as dimethyl formamide (see French Patent Specification No. 1,451,000), a lower alcohol or an ether (see German Patent Specification No. 1,670,214) or benzene. The known reaction is furthermore effected in the presence of an acid or basic catalyst, most generally a strongly basic catalyst such as a tertiary amine or alkali hydroxide.

This known method of preparation, however, has the disadvantage that the solvent or vehicle, as well as traces of the catalyst, must be removed from the reaction product upon completion of the reaction. Furthermore, the product is obtain in the solid state, and in order to be used as a polyol in the preparation of polyurethane, it must be again dissolved in the other reactants.

It is an object of the present invention to provide a process for the preparation tris-(β-hydroxypropyl) isocyanurate by the reaction of cyanuric acid with propylene oxide without the need for the presence of a catalyst. It is a further object of this invention to provide a process whereby the reaction product is obtained in a form directly usable as a polyol in the preparation of polyurethane without the need for separation and/or redissolution of the solid product.

BRIEF DESCRIPTION OF THE INVENTION

Tris-(β-hydroxypropyl) isocyanurate is prepared according to the present invention by the reaction of cyanuric acid with propylene oxide at a temperature between about 100° and 150° C. The reaction is carried out at a superatmospheric pressure, without the need for a catalyst, in the presence of a polyhydroxy compound that is liquid at the reaction temperature, and in which the tris-(β-hydroxypropyl) isocyanurate is soluble, and with which it is miscible. The reaction product thus formed may be directly utilized as a polyol in the preparation of polyurethane. It has been found that the conversion of cyanuric acid into tris-(β-hydroxypropyl) isocyanurate can be effected by the present process in a comparatively short time without appreciable formation of by-products. The reaction terminates upon addition of three hydroxy propyl groups to the isocyanurate ring without substantial propoxylation of the polyhydroxy compound or polyol used as the reaction medium or vehicle. It has also been found that when the reaction is carried out in accordance with the process of the present invention, no appreciable further propoxylation of the tris-(β-hydroxypropyl) isocyanurate occurs, even when excess propylene oxide is used.

DESCRIPTION OF PREFERRED EMBODIMENT

The polyhydroxy compound suitable for use in the present process may be any of those compounds that are liquid at the reaction temperature, with which tris-(β-hydroxypropyl) isocyanurate is miscible or in which it is soluble, and which polyhydroxy compound can be used as a polyol, in addition to tris-(β-hydroxypropyl) isocyanurate, in the preparation of polyurethane. Examples of suitable types of polyhydroxyl compounds for use in this process are aliphatic and cycloaliphatic polyols with 2 to 15 carbon atoms, polyoxyalkylene glycols derived from ethylene oxide, propylene oxide or butylene oxide with 2 to 20 oxyalkylene units; adducts of a $C_2$–$C_4$ alkylene oxide to a $C_2$–$C_{12}$ aliphatic, cycloaliphatic or aromatic polyamino or monohydroxymonoamino compound, or to a $C_{2-15}$ aliphatic or cycloaliphatic polyol or to cyanuric acid, the said adducts containing 1 to 10 oxyalkylene units per hydroxyl or aminogroup.

Specific examples of such suitable polyhydroxy compounds include diethylene glycol, triethylene glycol, dipropylene glycol, adducts of ethylene oxide and/or propylene oxide to ethylene diamine, diamino butane, isophorone diamine, or toluene diamine. It is also possible to utilized a mixture of water and a diamino compound or a polyamine as the reaction medium, wherein the amino hydrogen atoms are replaced in situ by a hydroxypropyl group. Other polyhydroxy compounds that may be used as the reaction medium in the present invention are trihydroxy compounds, such as trifunctional aliphatic alcohols, including glycerol and trimethylol propane, and adducts of an alkylene oxide to a triamine or polyamine or trihydroxy compound, such as glycerol-ethylene oxide adduct or a propylene-oxide-diethylenetriamine adduct.

The process of the present invention should be carried out at a superatmospheric pressure, which has been found to reduce the formation of colored by-products. The pressure of reaction is suitably between about 2 and 20 bars, and most preferably between the vapor pressure of propylene oxide at the reaction temperature and 15 bars. At a lower pressure the reaction time is prolonged, and no advantageous effect is apparent if pressures higher than those noted above are utilized.

The reaction may be carried out at a temperature of between about 100° and 150° C., but most preferably between about 120° and 140° C.

The molar ratio of propylene oxide to cyanuric acid should be at least the stoichiometric amount required to convert all the cyanuric acid to tris-(β-hydroxypropyl) isocyanurate and preferably should be in the range of between about 3:1 and 5:1.

The cyanuric acid starting compound may be pure cyanuric acid, but crude cyanuric acid, containing, for instance, ammeline and ammelide, may be used as well. The amount of polyhydroxy compound serving as the reaction medium or vehicle should be between about 25 and 1,000 percent by weight relative to the amount of cyanuric acid present. Good results are obtained using about 25 to 500 percent by weight polyhydroxy compound, and preferably 50 to 200 percent by weight is used.

No catalyst need be present in order to effect the desired reaction to tris-(β-hydroxypropyl) isocyanurate and therefore there is no need to separate catalyst from the final reaction product. The fact that the present process is carried out in the absence of catalysts used in the known processes has the additional advantage that undesired further propoxylation is suppressed even in the presence of excess propylene oxide.

The reaction according to the present invention maybe carried out by several different procedural sequences. For example, the propylene oxide and the polyhydroxy vehicle may first be fed, followed by the addition of the cyanuric acid. Alternatively, the propylene oxide may be added to a dispersion of cyanuric acid in the polyhydroxy compound vehicle. It is also possible to carry out the reaction in two stages wherein a part of the cyanuric acid to be converted is reacted with propylene oxide to form a mixture of polyols in a first stage, which mixture of polyols can thereafter be used as the reaction medium for the conversion of an additional amount of cyanuric acid. Alternatively it is possible to propoxylate a mixture of cyanuric acid and a diamino or polyamino compound in the reaction medium formed in the first stage. The process can then be effective continuously, and the mixture of cyanuric acid and an amino compound can be converted into an mixture of polyols which can be directly used in the preparation of polyurethane. It is an advantage of the process of the present invention that the hydroxyl groups, once attached, are not subjected to further propoxylation. Consequently, the product has a constant composition even when excess propylene oxide is present during the reaction.

EXAMPLE I 92 grams of cyanuric acid were placed in a 1-liter autoclave together with 87.2 grams of an adduct of propylene oxide to ethylene diamine (hydroxyl number 480) as the reaction medium. 125 grams of propylene oxide were then added with stirring over a period of 4 hours at a temperature of 130°–135° C. Next, another 125 grams of propylene oxide and 92 grams of cyanuric acid were added in portions, with stirring, to the mixture in the autoclave. The propylene oxide was fed in at a pressure of 100 bars, and the pressure during the reaction varied from 2 to 15 bars. The final reaction product was a clear liquid consisting of 80% by weight of tris-($\beta$-hydroxypropyl) isocyanurate and 20% by weight of the reaction medium adduct of propylene oxide and ethylene diamine. Upon analysis it was found that no free cyanuric acid was present in the final reaction product and that no detectable further propoxylation of the ethylene diamine/propylene oxide adduct used as the reaction medium had occurred.

EXAMPLE II

Cyanuric acid was proproxylated in the manner described in Example I, except using an adduct of ethylene oxide to toluene diamine (hydroxyl number 400) as the reaction medium, to form a final reaction product mixture of 85% by eight of tris-($\beta$-hydroxypropyl) isocyanurate and 15% by weight of the adduct used as the reaction medium. The mixture had a hydroxyl number of 486, a viscosity at 71° C. of 43470 cP, and a specific gravity of 1.18 (20° C.).

EXAMPLE III

The process of Example I was repeated except using 87 grams of glycerol as the reaction medium and a reaction time of one hour in the first stage and two hours in the second stage. No appreciable propoxylation of the glycerol occurred and all cyanuric acid was converted.

EXAMPLE IV

At a temperature of 130° C. and a pressure of 15 bars, 4 moles of propylene oxide per mole of ethylene diamine and 3 moles of propylene oxide per mole of cyanuric acid were added to a suspension of ethylene diamine and cyanuric acid in water. The exothermal conversion reached completion after half an hour. Upon distillation at reduced pressure to a constant weight, to remove water, a mixture was obtained that considered of 2.8% by weight of water, 15% by weight of propylene oxide/ethylene diamine adduct, 5% by weight of propane diol and 72.2% by weight of tris-($\beta$-hydroxypropyl) isocyanurate. This mixture was suitable for use as a reaction medium in the propoxylation of cyanuric acid and, after further removal of water, as a polyol mixture in the preparation of polyurethane.

EXAMPLE V

A mixture of 101 grams of tris-($\beta$-hydroxypropyl) isocyanurate and 348 grams of propylene oxide was heated at 135° C. and a pressure of 24 bars for eight hours. Upon termination of the heating, the mixture was analysed and it was found that no appreciable propoxylation has occurred, and no by-products, such as oxazolidones, had formed.

EXAMPLE VI 144 grams of the product obtained in Example I were put in a 1-liter autoclave. 64.5 grams of cyanuric acid and 6 grams of ethylene diamine were added and, over a period of two hours, 110 grams of propylene oxide were added with stirring at a temperature of 130°–135° C. The propylene oxide was fed in at a pressure of 100 bars and the pressure in the autoclave during the reaction varied from 2 to 12 bars. A clear straw-colored liquid was obtained which contained no free cyanuric acid and no ethylene diamine. The composition of the reaction product thus obtained was 80% by weight of tris-($\beta$-hydroxypropyl) isocyanurate and 20% by weight of the adduct of ethylene diamine and propylene oxide. 144 grams of this reaction product were then again used for the propoxylation of cyanuric acid and ethylene diamine in the manner described above.

What is claimed is:

1. In a process for a preparation of tris-($\beta$-hydroxypropyl) isocyanurate by the reaction of propylene oxide and cyanuric acid at a temperature within the range of between 100° and 150° C., the improvement wherein said reaction is carried out at elevated pressure in the presence of a polyhydroxy compound reaction medium which is a liquid at the reaction temperature, in which said tris-($\beta$-hydroxypropyl) isocyanurate is soluble or with which it is miscible, said reaction being carried out in the absence of a catalyst.

2. The process of claim 1 wherein the amount of said polyhydroxy compound is between about 25 and 1,000 percent by weight relative to the amount of cyanuric acid.

3. The process of claim 2 wherein said polyhydroxy compound is present in an amount of between about 50 and 2000 percent by weight relative to the amount of cyanuric acid.

4. The process of claim 1 wherein said polyhydroxy compound is selected from the group consisting of (cyclo)aliphatic polyols with 2 to 15 carbon atoms, polyoxyalkylene glycols with 2 to 20 units derived from a $C_2$–$C_4$ alkylene oxide, adducts of an alkylene oxide to an aliphatic, cycloaliphatic or aromatic polyamino or monohydroxy-monoamino compound with 2 to 12 carbon atoms or to a (cyclo)aliphatic polyol containing 2–15 carbon atoms or to cyanuric acid the said adducts containing 1 to 10 oxyalkylene units per hydroxyl or amino group, and combinations thereof.

5. The process of claim 1 wherein said reaction is carried out at a pressure of between about 2 and 20 bars.

6. The process of claim 1 wherein a mixture of said propylene oxide and polyhydroxy compound is first formed whereafter said cyanuric acid is added to said mixture.

7. The process of claim 1 wherein, in a first stage, a portion of said cyanuric acid is reacted with propylene oxide to form a mixture of polyols and, in a second stage, said mixture of polyols serves as the reaction medium for the reaction of an additional portion of said cyanuric acid.

8. The process of claim 7 wherein, in said second stage, a mixture of cyanuric acid and a polyamino compound is propoxylated in said mixture of polyols from said first stage.

* * * * *